(12) United States Patent
Thomas

(10) Patent No.: US 6,488,920 B1
(45) Date of Patent: Dec. 3, 2002

(54) GRADUAL HAIR RELAXATION COMPOSITION

(75) Inventor: Lillie C. Thomas, Henderson, NV (US)

(73) Assignee: GT Merchandising & Licensing Corp., New York, NY (US)

( * ) Notice: Subject to any disclaimer, the term of this patent is extended or adjusted under 35 U.S.C. 154(b) by 0 days.

(21) Appl. No.: 09/615,443

(22) Filed: Jul. 13, 2000

Related U.S. Application Data

(63) Continuation of application No. PCT/US99/28729, filed on Dec. 2, 1999.
(60) Provisional application No. 60/110,611, filed on Dec. 2, 1998.

(51) Int. Cl.[7] .............................. A61K 7/06; A61K 7/09
(52) U.S. Cl. ..................... 424/70.1; 424/70.2; 424/70.5
(58) Field of Search ............................. 424/70.1, 70.2, 424/70.4, 70.5

(56) References Cited

U.S. PATENT DOCUMENTS

| | | | |
|---|---|---|---|
| 5,217,711 A | * | 6/1993 | De Oliveira |
| 5,635,168 A | * | 6/1997 | Burns et al. ............... 424/70.4 |
| 5,639,451 A | * | 6/1997 | Evans, Jr. et al. ....... 424/70.51 |
| 5,655,552 A | | 8/1997 | Samain |
| 5,690,956 A | | 11/1997 | Lau |
| 5,856,345 A | * | 1/1999 | Doi et al. |

OTHER PUBLICATIONS

The Merck Index (Merck Research Laboratories 1996) Sodium Thiosulfate, monograph 8844.*
Rene Furterer—Color–Treated– Permed, Relaxed Hair (online). {retrieved on Apr. 7, 2001}. Retrieved from the Internet <URL:http://www.renefurterer.com/Hair_Solutions/Color–Treated_And_Or_Permed_HA/body_color– treated_and_or_permed_ha.html>.*

* cited by examiner

Primary Examiner—Thurman K. Page
Assistant Examiner—Humera N. Sheikh
(74) Attorney, Agent, or Firm—Schweitzer Cornman Gross & Bondell LLP

(57) ABSTRACT

A hair relaxation composition is provided. The hair relaxation comprises an activator containing a thiosulfate compound, an acidifier that preferably does not impart a color change to the hair, and a catalyst. The composition has a pH ranging from about 3.0 to about 4.5. A method for relaxing hair is also provided. A composition as described above is applied to the hair. The composition is allowed to remain on the hair for a period of time ranging from about 10 minutes to about 60 minutes. The composition is removed from the hair. The application, standing and removal steps are then repeated.

16 Claims, No Drawings

GRADUAL HAIR RELAXATION COMPOSITION

CROSS-REFERENCE TO RELATED APPLICATION

This application claims priority of International Patent Application No. PCT/US99/28729, filed Dec. 2, 1999, which claims the benefit of U.S. Provisional Patent Application No. 60/110,611 filed Dec. 2, 1998, the entire disclosures of which are herein incorporated by reference.

BACKGROUND OF THE INVENTION

Hair straightening has been used by many ethnic populations to produce a smoother texture and straighter appearance for more than 100 years. The initial method for straightening involved hot irons and coating the hair in petroleum. The result of this "straightening" process often resulted in burning the hair off. If not, this produced "straight" hair styles which were short and over time caused the hair to break, resulting in shorter more brittle hair. This effect was amplified as straightening products were repeatedly used in the hair. The first commercial products, which have been available for over 70 years, were based on sodium hydroxide. While the amount of sodium hydroxide in the products has decreased over the years, the chemistry involved, and the methodology used has changed little over the years. Newer fixatives and conditioners have improved the texture of the hair to prevent some of the dry and brittle appearance that often results after long periods of using straighteners. However, the ability to grow long hair while straightening is still a difficult beauty challenge.

For the consumer with naturally curly hair, from a style perspective, the consumer either elects to have their hair "natural" leaving the curly texture of the hair as it is, or to use straightening products and have their hair "straight" without curl. The current commercial products do not provide the consumer the option to have a hair style which is "in between". An active life style which adds perspiration to the straightened hair can cause the relaxed hair to be dry, brittle and unmanageable. Extended use of the available straightening products can damage and weaken the hair resulting in hair that is short and brittle with little control.

There are two types of hair straightening products currently available in the U.S. cosmetic market. The first class is those based on a caustic "lye" formulation. The products in this class are sometimes labeled as "lye" or "no lye". The lye based products contain the active ingredient sodium hydroxide. This chemical is very alkaline and is the same ingredient contained in drain cleaners. Other products in this class are referred to as "no lye" but only contain a different positive cation with hydroxide producing the same class of alkali chemical. The most common are calcium hydroxide and potassium hydroxide. Calcium hydroxide is often used in plaster and cement, while potassium hydroxide can be extremely corrosive. These formulas are commonly used in the commercially available hair straighteners bought for home use. These products are easy to apply and have a long history of use. As strong alkali products, these formulations can cause severe burns and are very hazardous to skin scalp and mucus membranes. These products carry specific label warnings to avoid contact with the skin.

The second class of products are ammonium thioglycolate based, often referred to as "thio" straighteners or "perms". These products are also alkaline and are most commonly used by professional beauticians. Without careful use by a professional, these products can be a depilatory in addition to causing severe burns. This product was originally developed from the permanent wave.

Both of the current straightening methods work in the hair essentially the same way. Both classes soften the hair and cause a swelling action to the shaft, sometimes up to three times the diameter of the hair. The product penetrates into the cortical layer and the cross bonds of sulfur and hydrogen are broken. The action of the combs and or hands smoothing the hair distributes the chemicals and straightens the softened hair. The hydroxide content ranges between 2 and 10 percent and produces a pH of greater than 10 (often as high as 12 or 13). In the hair this is considered to be a strong alkali. The higher the pH the faster the chemical reaction initiates hair straightening, the greater the softening of the hair and the greater the damage that can be done to the hair. Ammonium thioglycolate works essentially the same way with a less dramatic action than the hydroxide based formulas, and is assumed by the cosmetologist to be gentler to the hair.

One particular drawback of the current commercial products is that they are caustic in nature, with a pH of greater than 10, which weakens the hair shaft and causes hair damage. Specifically, the pH of hair varies over the length of the strand between about 4.9 and about 6.2, with more acid at the scalp than at the tips of the hair. Disulfide bonds are not permanently affected at pH levels between 2 and 6, but salt bonds can be affected at pH levels below 4. This is why typical caustic prior art straighteners operate at pH levels above 10. The hair cannot buffer itself against pH changes, so it is important to control pH within a specified range in order to maintain effectiveness of the hair treatment product and prevent permanent hair damage. As hair cannot regenerate, only grow out, permanent damage to the hair can affect the individual for a long period of time.

Since hair in its normal state is slightly acidic, the use of an acid to straighten hair should provide more protection to the hair. Other attempts have been made to produce a product having an acidic pH. However, previous acid-based compositions change the color of light hair, such as blonde hair or grey hair, to either green or black. The hair can also be "bleached" out leaving it dry and brittle.

Additionally, traditional straightening compositions cause lanolization, i.e., produce hair that is permanently chemically altered and unable to reform the natural bonds. This process compromises the strength of the hair in order to produce the straight look. As a result, the hair cannot later be easily or safely styled with curls because the hair has lost its resilience. Further, traditional straightening products cause a permanent change in the hair chemistry, producing hair that is completely straight.

Further, traditional thio straightening product have a strong negative odor. The odor is difficult to mask, even with the addition of fragrance. Many consumers liken it to "rotten eggs".

SUMMARY OF THE INVENTION

The present invention is directed to a curl relaxation composition that attempts to overcome the above drawbacks. Instead of having a caustic or alkali formulation, the inventive composition is based on an acidic preparation that uses the natural hair chemistry to produce a more gradual and gentle straightening while adding combability and manageability to the hair. Additionally, the composition does not alter the natural color of the hair, even when applied to light hair, allowing safe application of the composition to red, blonde and grey hair.

Moreover, the composition does not chemically alter the hair. When applied to the hair, the inventive composition is at a pH that is slightly below the isoelectric point of keratin, the predominant protein in hair. This will temporarily break the disulfide and hydrogen bonds in the hair. This reaction, in combination with covering the hair during processing and smoothing the hair, will produce a straighter, more manageable appearance. When neutralized with a neutralizing shampoo, the disulfide bonds are restored and the hydrogen bonds are restored to the preferred a form, providing strength and durability during styling. The a form also provides shine and luster for the hair. The composition causes a permanent change in the curl of the hair without changing the hair chemistry. As a result, the composition of the present invention gradually relaxes the hair with repeated applications, allowing for more styling freedom. The inventive composition allows the hair to be safely smoothed and styled with curls while conditioning the hair for manageability and bounce. The hair has a more manageable texture, and the work required for combing decreases. This decreases mechanical damage to the hair, allowing its to remain healthier.

Further, preferred compositions in accordance with the invention are substantially odorless. Fragrances can be added to enhance the scent of the composition, but fragrance is not required to mask a negative odor associated with the composition.

In one embodiment, the invention is directed to a hair relaxation composition comprising an activator containing a thiosulfate compound, an acidifier, and a catalyst. The composition has a pH ranging from about 3.0 to about 4.5.

In another embodiment, the invention is directed to a hair relaxation composition comprising an activator containing a thiosulfate composition, an acidifier that does not impart a color change to the hair, and a catalyst.

In yet another embodiment, the invention is directed to a method for relaxing hair comprising applying to the hair one of the compositions described above.

In a particularly preferred embodiment, the invention is directed to a method for relaxing hair comprising applying to the hair one of the compositions described above. The composition is allowed to remain on the hair for a period of time ranging from about 10 minutes to about 60 minutes. The composition is then removed from the hair in a neutralizing process. The application, standing and removal steps are then repeated.

DETAILED DESCRIPTION

The present invention is directed to a composition and method for gradually relaxing hair. In one embodiment, the invention is directed to a composition comprising an activator containing a thiosulfate compound, an acidifier, and a catalyst.

The activator containing a thiosulfate compound is the active ingredient in the composition. The thiosulfate compound provides the necessary free sulfur for restructure of the disulfide bonds in the hair, allowing smoothing of the hair with a salt form that is most compatible with the hair. Preferred thiosulfate compounds include sodium thiosulfate, potassium thiosulfate and calcium thiosulfate. The activator is preferably present in an amount ranging from about 2% to about 35% by weight, more preferably from about 4% to about 10% by weight, based on the total weight of the composition.

The acidifier can be any suitable acidifier. Preferably the acidifier is a composition that does not impart a color change to the hair, such as citric acid or acetic acid. Suitable acidifiers for use in the inventive composition include citric acid, acetic acid, adipic acid, ascorbic acid, tartaric acid and tannic acid. The acidifier is present in the composition in a positive amount, preferably up to about 1.0% by weight based on the total weight of the composition. More preferably the acidifier is present in an amount ranging from about 0.2% to about 0.5% by weight based on the total weight of the composition. The acidifier is preferably provided in an amount such that the final composition has a pH ranging from about 3.0 to about 4.5, more preferably from about 3.3 to about 3.8.

A catalyst is provided in the composition to initiate the chemical reaction, allowing for the change in the disulfide bonds. As discussed in more detail below, prior to use, the catalyst is maintained separate from the activator, as is known in the art. The catalyst can be any suitable catalyst known to those skilled in the art. Preferably the catalyst is a chloride compound, such as zinc chloride, manganese chloride, or magnesium chloride, all minerals found naturally in hair. Preferably the catalyst is selected so as not to impart a color change to the hair and to be compatible with hair chemistry. The catalyst is present in the composition in a positive amount, preferably up to about 1.5% by weight based on the total weight of the composition. More preferably the catalyst is present in an amount ranging from about 0.2% to about 0.5% by weight based on the total weight of the composition. The amount of catalyst is selected based on the weight of the activator.

The composition preferably further comprises a filler to impart texture and thickness to the composition. The filler can be any suitable filler such as, for example, corn starch, talc, maltrin, carboxymethylcellulose gum or carboxyethylcellulose gum. Preferably the filler is present in the composition in an amount ranging from about 5% to about 40% by weight, more preferably from about 15% to 25% by weight, based on the total weight of the composition. As would be recognized by one skilled in the art, the amount of filler can vary as desired to provide the desired feel for the composition, which can be in any suitable form, such as liquid, gel, cream or paste form. Depending on the filler used, a thickening agent may be added to form the creme for the application texture. The application texture is a human factor consideration for easy application.

Additionally, the composition can contain any other suitable additives typically used in hair care compositions. Examples of such additives include, but are not limited to, fragrances, biocides (such as propylparaben), and fungicides (such as methylparaben), and nutrients (such as ascorbic acid and Vitamin E).

The remainder of the composition is water. As is known in the art, such compositions are traditionally provided in powdered form, with two distinct components so that the catalyst is separate from the activator. All ingredients are carefully blended and provided with a particle size sufficient to form a consistent powder that is easily hydrated in water. The powdered components can be combined together with water prior to use to form a composition of the desired consistency for the consumer.

The invention is also directed to a method for gradually relaxing, and optionally straightening, hair. According to the method the hair is cleaned and separated into sections. If desired, conditioner is applied at the hair line to prevent irritation, although the inventive composition is not particularly irritating, and thus conditioner is not necessary. Working with each section of hair individually, the user applied hair relaxation composition described above to the hair from root to end with the finger tips or a comb, spreading the mixture uniformly until all of the hair is saturated. After application, the hair is positioned as straight as possible, with longer hair being wrapped around the head. After the head is completely covered with the relaxation composition, it is covered with a plastic shower cap. Application time will vary depending on the porosity of the hair, as would be recognized by one skilled in the art, but is generally between about 20 and 60 minutes, preferably between 30 and 50 minutes. Typically, after 50 minutes the catalyst is used up, and thus further application time has little if any effect.

The hair is then rinsed thoroughly with warm water. During application with the inventive composition, the pH of the hair, which is normally between 5.5 to 6.0, is lowered to about 3.5 to 4. Accordingly, the hair is washed with a neutral pH balancing shampoo to restore the hair's natural pH. The pH balancing shampoo should have a pH ranging from about 5.5 to about 7.0, preferably from about 5.5 to 6.5, which is close to the hair's natural pH. If the shampoo has a higher pH, e.g., greater than 7.0, it can cause the hair to become brittle, or even break the hair. A suitable shampoo for use in accordance with the invention is Copa pH Balancing Shampoo, commercially available from Copa (Irvine, Calif.). Preferably a conditioner, optionally one with a compatible pH balancing effect, is also applied to the hair and allowed to remain on the hair for about 3 to 5 minutes.

The hair is then dried, either naturally or with a controlled moderate heat dryer. During the drying process, the hair can be stretched for further straightening, or curlers can be applied to style the hair.

Due to time constraints, preferably no more than two applications of the relaxation composition are initially applied. The first one to two applications condition the hair and provide a conditioned wave. If a straighter style is desired, additional applications can be provided. Preferably, three to five applications are provided. Further applications should be provided to new hair growth approximately every four to six weeks; however, for new hair growth only one application is typically necessary because the composition is concentrated on a smaller section of hair. During this reapplication, the inventive composition will not harm the old hair growth, on which it was previously applied.

EXAMPLES

Preparation of Composition

A hair relaxation composition in accordance with the invention was prepared as follows. Two dry mix packets were prepared, a complex and an activator, each having the following compositions:

| Complex | |
|---|---|
| Sodium thiosulfate | 42.5% |
| Maltodextrin | 26.7% |
| Modified food starch | 25.0% |
| Carboxymethylcellulose (CMC) gum | 3.5% |
| Citric acid | 1.7% |
| Fragrance | 0.25% |
| Methylparaben | 0.20% |
| Propylparaben | 0.10% |
| Activator | |
| Maltodextrin | 52.4% |
| Modified food starch | 25.0% |
| Ammonium chloride | 20.1% |

| -continued | |
|---|---|
| Manganese chloride | 2.0% |
| Fragrance | 0.25% |
| Methylparaben | 0.20% |
| Propylparaben | 0.10% |
| Ascorbic acid | 0.01% |
| Vitamin E acetate | 0.01% |

Prior to each experiment, the composition was prepared from the two dry mix packets (complex and activator) in a 1000 ml. beaker with the addition of 177 ml. of water at 25° C. The product was manually stirred with a fork, the most difficult method of preparation, and with the coolest temperature recommended as this too adds to the difficultly in assuring that the mixture was homogeneous. These methods provided the potential for the least homogeneous mix, thus most closely simulating the worst consumer conditions.

The final preparation had the following composition (where are amounts are indicated as weight percent based on the total weight of the composition):

| | |
|---|---|
| Filler | 18.8% |
| maltodextrin (11.2%) | |
| food starch (7.1%) | |
| CMC gum (0.5%) | |
| Fragrance | 0.08% |
| Fungicide (methylparaben) | 0.06% |
| Biocide (propylparaben) | 0.02% |
| Catalyst | 3.12% |
| ammonium chloride (2.8%) | |
| manganese chloride (0.28%) | |
| Acidifier (citric acid) | 0.24% |
| Activator (sodium thiosulfate) | 6.0% |
| Nutrients | 0.003% |
| Vitamin E acetate (0.001%) | |
| Ascorbic acid (0.002%) | |
| Water | 72.7% |

The composition met the following parameters:

Color: White

Granulation: 80% through a 60 mesh sieve pH at 30°±2° C. at preparation: 3.5±0.3 pH at 30°±2° C. at 60 minutes: 3.5±0.3

Activator pH at 30°±2° C.: 3.5±0.5

Complex pH at 30°±2° C.: 4.0±0.5

Sodium assay, combined: between 1.04% and 1.27%

Sodium assay, activator: between 1.20 and 1.46%

Manganese, combined: between 0.070% and 0.086%

Manganese, complex: between 0.081% and 0.099%

Specific gravity, complex: between 0.502 gm/ml and 0.614 gm/ml

Specific gravity, activator: between 0.376 gm/ml and 0.459 gm/ml

Evaluation of Tensile Strength

This experiment evaluated the effect of the inventive composition on virgin hair and hair that has been pre-treated with tints, treated with permanents (thio-based with peroxide neutralizer), relaxed (sodium hydroxide) and bleached. The purpose of this test is to quantitatively measure the elasticity of hair, which is subjective, in terms of an objective parameter, namely, tensile strength. The test quantified the strength that the test hair exhibited up to the breakage of the individual strand.

Tensile strength is defined as the capability of a material to withstand stress imposed when it is stretched or elongated. Styling of the hair tests the tensile strength continuously as the act of pulling a comb or brush through the hair elongates and stretches the hair for smoothing purposes. In styling applications, the most common measure of tensile strength is the elasticity of the hair, which is subjectively measured by the ability of the hair to stretch and return to its original length.

Tensile strength can vary. Because there is much individual variation in hair tensile properties, a base reading prior to any application of a hair treatment product was established on virgin hair and pre-treated hair and used as a control value for each individual hair sample.

The hair involved in this study was purchased test hair. The purchased grey hair and brown hair were treated with various commercial chemical preparations (perms, relaxers, tinting, bleach). These samples were then over-applied with the inventive composition, described above, three times. Normalization samples were collected and tested for tensile strength. These samples were collected to be compared to the test hair for differences, and used to adjust results to make test results reflective of African American hair. The test hair was tested for tensile strength. Hair samples were provided in 8-inch lengths and stored at room temperature.

Since there is so much individual variation in hair tensile properties, a base reading of the samples was collected and used as the control reading to compare all of the competitive applications of straightening products. All products were used only on the samples of hair purchased. All hair was in the same condition.

For each sample, consistent with accepted laboratory procedure, a minimum of three trials were performed to determine the final reading of tensile strength. The individual strands of hair were chosen at random from the test sample. Wet and dry hair samples were tested. Wet samples were pre-soaked at room temperature in distilled water for 24 hours, then placed in the test instrument wet, as described below.

The commercial chemical products used to treat the hair were generally available in interstate commerce and typical of products used by cosmetologists to provide the chemical services to be tested (perm, relaxation, tinting, and bleaching). These products were applied according to packaging instructions by a licensed cosmetologist. For the inventive composition, the application process was repeated three separate times. Each time the product was applied, it was prepared fresh. Treatments 2 and 3 were applied with no rest in between, i.e., on a "back to back" basis. The application frequency used in this study was the harshest conditions, and thus provided the best estimation of the incorporation of human factors into the application process.

Each product was applied to dry hair and smoothed with the fingers. During the treatment period, the hair was covered in plastic bags to simulate actual treatment conditions required by the instructions.

Post treatment, all samples were washed as directed using the provided neutralizing shampoo. After the hair was neutralized, all samples of hair were blown dry with a commercial hair dryer on high heat, using brushes and combs to simulate the rough handling that could potentially be part of a consumer's beauty care program. The brush was a plastic toothed brush, not generally used by ethnic populations. It is harsher to the hair than a boars hair brush (generally used), and could produce more structural damage, thus creating the worst conditions. High heat, although not recommend for use in connection with the inventive composition, is the worst case for consumer use of the products. The structure of the hair handling in this study was designed to incorporate the worst case human factors that could be created.

After all applications were completed and the hair was dry, samples were randomly collected (three hairs per sample) and bagged by pulling the hair sample and collecting those that fell out. These hairs would be the weakest of the total sample. Each sample was marked for identification and stored at room temperature.

Tensile readings were measured in pounds using appropriate load cells according to Nelson Laboratories Inc. Standard Operating Procedures for tensile testing on an INSTRON 1011 Physical Test Instrument (commercially available from Instron, Inc., Boston, Mass.). Each strand of hair being tested was placed into the grips of the INSTRON test instrument. Enough material was provided to cover the gauge length and to fit securely between the grips. Each independent sample was tested in accordance with the procedures described in the INSTRON Series IX Automated Materials Testing System Version 5, Issue B, November 1990 Reference Guide and User's Guide. The cross head speed was set to 20 inches per minute with the full scale load set to 100% using a ten pound load cell. The specimens were placed into the friction grips for testing. Prior to testing, all samples were pulled by one operator setting up the INSTRON per accepted protocols for the instrument to assure that the INSTRON was set up properly and treated each sample the same. Control samples were pulled first.

For each sample, three readings of the force necessary to break the hair were taken and averaged. This procedure was repeated for each test sample.

A rack was built to allow the hair to hang free and allow for combing and brushing during the styling and drying process. The commercial hair purchased was sewn together on a band across the top. The band was used to clip the hair to the rack to allow the length of the hair to hang free.

All experimental data was analyzed using the Student's t test. These statistical methods show differences in the treatments and the effects that the treatments have on the hair. All statistics were considered significant at $p \leq 0.05$. All results were considered insignificant at $p \geq 0.10$. Results that fell in between were considered to be inconclusive. All tensile strength data was measured in pounds. The sign of the t result is reflective of whether the hair is becoming stronger or weaker. The results of the testing are shown in Table 1 below.

TABLE 1

| Sample | Control | Inventive Composition |
| --- | --- | --- |
| Grey Untreated (Virgin) | .1664 | .1847 |
| Wet Grey Untreated (Virgin) | .1752 | .148 |
| Brown Untreated (Virgin) | .1936 | .2094 |
| Wet Brown Untreated (Virgin) | .1791 | .1644 |
| Brown Tinted | .2157 | .2194 |
| Wet Brown Tinted | .1847 | .174 |
| Grey Tinted | .1486 | .1715 |
| Wet Grey Tinted | .1673 | .1568 |
| Grey Permed | .1622 | .1765 |
| Wet Grey Permed | .1444 | .1364 |
| Brown Permed | .2003 | .1734 |
| Wet Brown Permed | .1955 | .1621 |
| Grey Relaxed | .1442 | .1918 |
| Wet Grey Relaxed | .1464 | .1514 |
| Brown Relaxed | .200 | .2193 |
| Wet Brown Relaxed | .1732 | .1847 |
| Grey Bleached | N/A | .1846 |
| Wet Grey Bleached | N/A | .1605 |
| Brown Bleached | N/A | .214 |
| Wet Brown Bleached | N/A | .1632 |

The standard deviations of the various treatments were consistent, indicating that the method was consistent, and the data indicated in detailed statistical testing that there was no significant difference at $p \leq 0.05$ between the various control treatments of the hair and the hair treated with the inventive composition after 3 applications.

The results of this experiment demonstrate the inventive composition does not damage the tensile strength of the hair.

For those hair samples that had been treated with relaxers and perms, the data indicates that the inventive composition was capable of restoring some of the tensile strength back to the relaxed and permed hair which had been removed during the previous chemical processes. This conclusion is consistent with the mechanism of how the inventive composition works.

The data further indicates that the inventive composition is compatible with relaxers, tints and bleachers. Further, the "wet" data is consistent with the general weakening of the hair in the wet state. Water, the universal solvent, dissolves the hydrogen bonds in the hair, leaving the hair weaker. The lower wet tensile strength values are consistent across the various treatments.

pH Stability

The purpose of this experiment was to verify that the pH of the inventive composition remains within the desired pH range. This experiment compared the pH of the hair treatment composition at the time of reconstitution and over 1 hour to determine whether any change in the pH occurs over the course of a single application of the composition.

Three identical composition samples were individually prepared as described above. The pH of the water used to prepare each composition sample was measured and recorded, and is shown in Table 2 below. For each composition sample, three trials were performed to determine the final pH reading. Each sample was tested at room temperature and held at room temperature for the duration of the test. Sample readings were taken in triplicate every ten minutes for 1 hour on an IQ Scientific Portable pH Meter (commercially available from IQ Scientific, San Diego, Calif.) in accordance with the procedure described in the IQ Scientific pH Meter Manual and Calibration Method. Room temperature was about 20.4° C. Lab replications took an average of about 4 minutes to complete. In between readings, the probe was normalized in pH 4.0 buffer. The results are shown in Table 2 below.

times (i.e., five single applications back to back) and a consecutive swatch from each application was retained for color comparison. The samples were tested and held at room temperature for the duration of the test. The results of the test are shown in Table 3 below.

TABLE 3

| Sample | Composition | pH | Result |
|---|---|---|---|
| Sample A | Ascorbic acid with manganese | 3.5 | Straightened, but bleached the hair |
| Sample B | Ascorbic acid with sodium thiosulfate | N/A | Discolored hair after one application (bleached) |
| Sample C | Ascorbic acid, sodium thiosulfate and manganese sulfate | 3 | After three applications, the hair was weakening |
| Sample D | Ascorbic acid and cupric chloride | N/A | Hair converts to green after one application |
| Sample E | Ascorbic acid, sodium thiosulfate and manganese chloride | 4.0 | After four applications, hair bleaches somewhat |
| Sample F | Sodium thiosulfate and manganese chloride | 6.0 | No color change; hair was strengthening after repeated applications, limited straightening |
| Sample G | Citric acid, sodium thiosulfate, manganese chloride | 3.5 | No color change; hair strengthened and straightened. |

Safety Testing

This experiment was conducted to assure that the inventive composition is recognized by the U.S. Food and Drug Administration (FDA) as safe. The establishment of safety involves primary ocular and primary dermal irritation testing. These tests have established protocols, which are codified at 16 C.F.R. §1500.41 (dermal) and §1500.42 (ocular) [Federal Hazardous Substances Act Regulations], which are incorporated herein by reference. The tests were conducted and the results were as follows.

Dermal

Six New Zealand white rabbits each received a single dermal application of 0.5 ml of the inventive composition, prepared as described above, on two test sites, one abraded and one non-abraded. The tests sites were occluded for 24 hours and were observed individually for erythema, edema,

TABLE 2

| Sample | 10 Min. | 20 Min. | 30 Min. | 40 Min. | 50 Min. | 60 Min. | Average |
|---|---|---|---|---|---|---|---|
| 1 (Water pH 6.88 @ 24° C.) | 3.45 (24° C.) | 3.54 (23.8° C.) | 3.59 (23.2° C.) | 3.61 (23.1° C.) | 3.64 (23.1° C.) | 3.59 (23.1° C.) | 3.57 |
| 2 (Water pH 6.91 @ 23.7° C.) | 3.43 (23.5° C.) | 3.54 (23.5° C.) | 3.60 (23.1° C.) | 3.57 (23.0° C.) | 3.62 (23.0° C.) | 3.60 (23.0° C.) | 3.56 |
| 3 (Water pH 7.0 @ 24.3° C.) | 3.43 (23.8° C.) | 3.52 (23.8° C.) | 3.55 (23.7° C.) | 3.62 (23.6° C.) | 3.66 (23.8° C.) | 3.62 (23.7° C.) | 3.57 |
| Average | 3.44 | 3.53 | 3.58 | 3.60 | 3.64 | 3.60 | 3.57 |

Coloration Study

The coloration study verified the lack of color change that takes place after repeated applications of a composition in accordance with the invention.

Seven sample compositions were prepared where the ingredients and pH varied as indicated in Table 3 below. Each sample composition was applied to a sample of grey virgin hair. Grey hair was used because it is the most sensitive to color changes. Each hair sample was treated five and other effects 24 and 72 hours after application. Means scores from the 24 and 72 hour readings were averaged to determine the primary irritation index. A primary irritation index of 5 or more indicates a primary dermal irritant. A primary irritation index of 0.1 to 0.9 indicates potential for slight irritation, but rarely irritating to people and no warning required. The inventive composition exhibited a primary irritation index of 0.58, indicating that the inventive composition is not a dermal irritant according to the Federal Hazardous Substances Act Regulations.

Ocular

Six New Zealand white rabbits, free from visible ocular defects, each received a single intraocular application of 0.1 ml of the inventive composition, prepared as described above, in one eye. The contralateral eye, remaining untreated, served as a control. The eyes of all animals remained unwashed for 24 hours. Observations of corneal opacity, iritis, and conjunctivitis were recorded 24, 48 and 72 hours after treatment. A score of 0 indicates no irritation, 1 to 4 minimal irritation, 5 to 8 mild irritation, 9 to 11 moderate irritation and 12 to 16 severe irritation. A test using Johnson's Baby Shampoo resulted in a score of 2.0 after 72 hours. The average scores for the inventive composition were 1.0 after 24 hours, 0.7 after 48 hours, and 0.0 after 72 hours, indicating that the inventive composition is not an ocular irritant according to the Federal Hazardous Substances Act Regulations.

The invention has been described in preferred and exemplary embodiments and aspects, but is not limited thereto. Persons skilled in the art will appreciate that other modifications and applications fall within the scope of the invention.

What is claimed is:

1. A hair relaxation composition to be applied as such to the hair, consisting essentially of:
   an activator containing a thiosulfate compound;
   an acidifier; and
   a catalyst,
   wherein the composition has a pH ranging from about 3.0 to about 4.5 and does not change hair chemistry.

2. A composition according to claim 1, wherein the composition has a pH ranging from about 3.3 to about 3.8.

3. A composition according to claim 1, wherein the thiosulfate compound is selected from the group consisting of sodium thiosulfate, potassium thiosulfate, and calcium thiosulfate.

4. A composition according to claim 1, wherein the thiosulfate compound is sodium thiosulfate.

5. A composition according to claim 1, wherein the acidifier is selected from the group consisting of citric acid, ascorbic acid, adipic acid, acetic acid, tartaric acid, and tannic acid.

6. A composition according to claim 1, wherein the acidifier is selected from the group consisting of citric acid and acetic acid.

7. A composition according to claim 1, wherein the catalyst comprises a chloride compound.

8. A composition according to claim 1, wherein the catalyst is selected from the group consisting of zinc chloride, manganese chloride, and magnesium chloride.

9. A composition according to claim 1, wherein the composition is substantially odorless.

10. A hair relaxation composition to be applied as such to the hair, consisting essentially of:
    an activator containing a thiosulfate composition;
    an acidifier that does not impart a color change to the hair; and
    a catalyst;
    wherein said composition does not change hair chemistry.

11. A method for relaxing hair comprising applying to the hair a composition according to claim 1.

12. A method for relaxing air comprising:
    (a) applying to the hair a composition according to claim 1;
    (b) allowing the composition to remain on the hair for a period of time ranging from about 10 minutes to about 60 minutes;
    (c) removing the composition from the hair; and
    (d) repeating steps (a) through (c).

13. A method according to claim 12, further comprising applying heat to the hair for at least a portion of the period of time.

14. A method according to claim 12, wherein the composition has a pH ranging from about 3.3 to about 3.8.

15. A method according to claim 12, wherein the color of the hair is not altered.

16. A method according to claim 12, wherein the treated hair is rinsed with water, and the hair is then treated with a neutral pH balancing shampoo to restore the hair's natural pH.

* * * * *